United States Patent [19]

Lindberg et al.

[11] Patent Number: 5,430,042
[45] Date of Patent: Jul. 4, 1995

[54] DIALKOXY-PYRIDINYL-BENZIMIDAZOLE DERIVATIVES, PROCESS FOR THEIR PREPARATION AND THEIR PHARMACEUTICAL USE

[75] Inventors: Per L. Lindberg, Askim; Gunnel E. Sundén, Göteborg, both of Sweden

[73] Assignee: Aktiebolaget Astra, Sodertalje, Sweden

[21] Appl. No.: 718,188

[22] Filed: Jun. 20, 1991

[30] Foreign Application Priority Data

Jun. 20, 1990 [SE] Sweden ................ 9002206
Jun. 20, 1990 [SE] Sweden ................ 9002207

[51] Int. Cl.6 .................. C07D 401/12; A61K 31/44
[52] U.S. Cl. .................. 514/338; 514/302; 546/271; 546/115
[58] Field of Search ........... 546/271, 115; 514/302, 514/338

[56] References Cited

U.S. PATENT DOCUMENTS

| | | | |
|---|---|---|---|
| 4,255,431 | 3/1981 | Junggren et al. | 514/338 |
| 4,686,230 | 8/1987 | Rainer et al. | 546/271 |
| 4,965,269 | 10/1990 | Brändström et al. | 546/271 |
| 5,019,584 | 5/1991 | Brändstrom et al. | 546/271 |
| 5,021,433 | 6/1991 | Alminger et al. | 514/338 |

FOREIGN PATENT DOCUMENTS

| | | |
|---|---|---|
| 0176308 | 4/1986 | European Pat. Off. . |
| 0221041 | 5/1987 | European Pat. Off. . |
| 0279149 | 8/1988 | European Pat. Off. . |

OTHER PUBLICATIONS

Haakanson et al. CA 112: 91794g, 1990.

Primary Examiner—Jane T. Fan
Attorney, Agent, or Firm—White & Case

[57] ABSTRACT

The novel compounds of the formula I

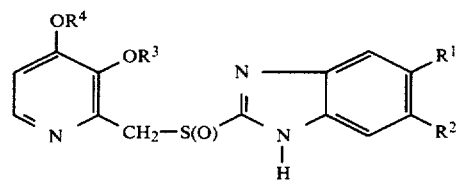

and physiologically acceptable salts thereof, wherein $R^1$ and $R^2$, which are different is each H alkyl containing 1-4 carbon atoms or $-C(O)-R^5$;

wherein $R^5$ is alkyl containing 1-4 carbon atoms or alkoxy containing 1-4 carbon atoms and one of $R^1$, or $R^2$ is always selected from the group $-C(O)-R^5$;

$R^3$ and $R^4$ are the same or different and selected from

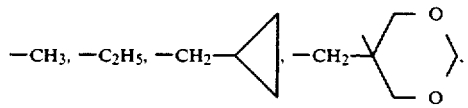

and $-CH_2CH_2OCH_3$ or $R^3$ and $R^4$ together with the adjacent oxygen atoms atached to the pyridine ring and the carbon atoms in the pyridine ring form a ring, wherein the part constituted by $R^3$ and $R^4$ is $-CH_2CH_2CH_2-$, or $-CH_2-CH_2-$ or $-CH_2-$; as well as intermediates, pharmaceutical compositions containing such compounds as active ingredient and the use of the compounds in medicine.

7 Claims, No Drawings

DIALKOXY-PYRIDINYL-BENZIMIDAZOLE DERIVATIVES, PROCESS FOR THEIR PREPARATION AND THEIR PHARMACEUTICAL USE

DESCRIPTION

1. Field of the invention

The object of the present invention is to provide novel compounds, and therapeutically acceptable salts thereof, which inhibit exogenously or endogenously stimulated gastric acid secretion and thus can be used in the prevention and treatment of peptic ulcer.

The present invention also relates to the use of the compounds of the invention, and therapeutically acceptable salts thereof, for inhibiting gastric acid secretion in mammals including man. In a more general sense, the compounds of the invention may be used for prevention and treatment of gastrointestinal inflammatory diseases, and gastric acid-related diseases in meals including man, such as gastritis, gastric ulcer, duodenal ulcer, reflux esophagitis, and Zollinger-Ellison syndrome. Furthermore, the compound may be used for treatment of other gastrointestinal disorders where gastric antisecretory effect is desirable e.g. in patients with gastrinomas, and in patients with acute upper gastrointestinal bleeding. They may also be used in patients in intensive care situations, and pre- and postoperatively to prevent acid aspiration and stress ulceration. The compounds of the invention may also be used for treatment or prophylaxis of inflammatory conditions in mammals, including man, especially those involving lysozymal enzymes. Conditions that may be specifically mentioned are rheumatoid arthritis and gout. The compounds may also be useful in the treatment of diseases related to bone metabolism disorders as well as the treatment of glaucoma. The invention also relates to pharmaceutical compositions containing the compounds of the invention, or a therapeutically acceptable salt thereof, as active ingredient. In a further aspect, the invention relates to processes for preparation of such new compounds, to novel intermediates in the preparation of the compounds of the invention, and to the use of the active compounds for the preparation of pharmaceutical compositions for the medical use indicated above.

It is a specific primary object of the invention to provide compounds with a high level of bioavailability. The compounds of the invention will also exhibit high stability properties at neutral pH and a good potency in regard to inhibition of gastric acid secretion. In addition the compounds of the invention will not block the uptake of iodine into the thyroid gland. It has earlier been disclosed in several lectures from the company, where the inventors are working that thyroid toxicity depends on if the compounds are lipophilic or not. The inventors have now unexpectedly found that it is not the lipophilicity that is the critical parameter. The claimed compounds, which include rather hydrophilic compounds, do not give any thyroid toxic effect and have at the same time high acid secretion inhibitory effect, good bioavailability and stability.

2. Prior Art and Background of the Invention

Benzimidazole derivatives intended for inhibiting gastric acid secretion are disclosed in numerous patent documents. Among these can be mentioned GB 1 500 043, GB 1 525 958, U.S. Pat. No. 4,182,766, U.S. Pat. No. 4,255,431, U.S. Pat. No. 4,599,347, EP 124 495, BE 898 880, EP 208 452 and Derwent abstract 87-294449/42. Benzimidazole derivatives proposed for use in the treatment or prevention of special gastrointestinal inflammatory diseases are disclosed in U.S. Pat. No. 4,359,465.

THE INVENTION

It has been found that the compounds of the following formula I show high bioavailability. The compounds of the formula I also are effective as inhibitors of gastric acid secretion in mammals and man and do not block the uptake of iodine into the thyroid gland. The compounds of the invention exhibit a high chemical stability in solution at neutral pH.

The compounds of the invention are of the following formula I:

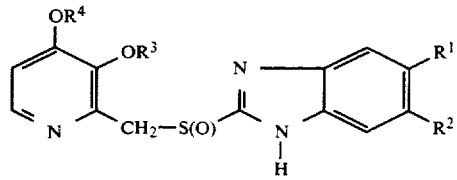

and physiologically acceptable salts thereof
wherein $R^1$ and $R^2$, which are different, is each H, alkyl containing 1-4 carbon atoms or $-C(O)-R^5$; wherein one of $R^1$ or $R^2$ is always selected from the group $-C(O)-R^5$; and wherein $R^5$ is alkyl containing 1-4 carbon atoms or alkoxy containing 1-4 carbon atoms;

$R^3$ and $R^4$ are the same or different and selected from

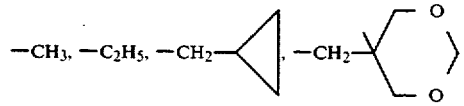

and $-CH_2CH_2OCH_3$ or $R^3$ and $R^4$ together with the adjacent oxygen atoms attached to the pyridine ring and the carbon atoms in the pyridine ring form a ring, wherein the part constituted by $R^3$ and $R^4$ is $-CH_2CH_2CH_2-$, $-CH_2CH_2-$ or $-CH_2-$.

It should be understood that the expressions "alkyl" and "alkoxy" include straight and branched structures.

The compounds of the invention of the formula I have an asymmetric centre in the sulfur atom, i.e. exist as two optical isomers (enantiomers), or if they also contain one or more asymmetric carbon atoms the compounds have two or more diastereomeric forms, each existing in two enantiomeric forms.

Both the pure enantiomers, racemic mixtures (50% of each enantiomer) and unequal mixtures of the two are within the scope of the present invention. It should be understood that all the diasteromeric forms possible (pure enantiomers or racemic mixtures) are within the scope of the invention.

Preferred groups of compounds of the formula I are:

1. Compounds, wherein $R^1$ and $R^2$ are selected from H methyl or $-C(O)R^5$ wherein $R^5$ is alkyl containing 1-4 carbon atoms or alkoxy containing 1-4 carbon atoms.

2. Especially preferred benzimidazole structures are

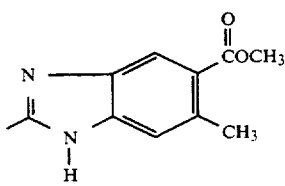

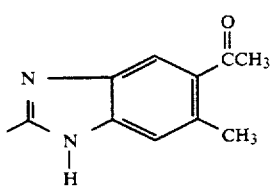

3. Compounds wherein $R^3$ and $R^4$ are $CH_3$.
4. Compounds wherein $R^3$ and $R^4$ together with the adjacent oxygen atoms attached to the pyridine ring and the carbon atoms in the pyridine ring form a ring wherein the part constituted by $R^3$ and $R^4$ is $-CH_2CH_2CH_2-$, $-CH_2CH_2-$ or $-CH_2-$.
5. Especially preferred pyridine structures are

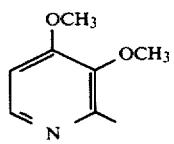

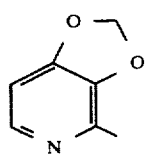

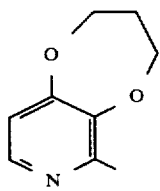

6. Further especially preferred specific compounds of the invention are as listed in the following tabulation.

| $R^1$ | $R^2$ | $R^3$ | $R^4$ |
|---|---|---|---|
| C(O)OCH₃ | CH₃ | CH₃ | CH₃ |
| C(O)CH₃ | CH₃ | CH₃ | CH₃ |
| C(O)OCH₃ | CH₃ | —CH₂— | |
| C(O)CH₃ | CH₃ | —CH₂CH₂CH₂— | |

Preparation

The compounds of the invention may be prepared according to the following method:

Oxidizing a compound of the formula II

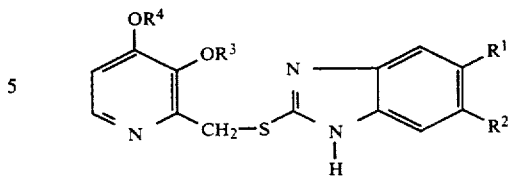

wherein $R^1$, $R^2$, $R^3$ and $R^4$ are as defined under formula I. This oxidation may be carried out by using an oxidizing agent such as nitric acid, hydrogen peroxide, (optionally in the presence of vanadium compounds), peracids, peresters, ozone, dinitrogentetraoxide, iodosobenzene, N-halosuccinimide, 1-chlorobenzotriazole, t-butylhypochlorite, diazabicyclo-[2,2,2]-octane bromine complex, sodium metaperiodate, selenium dioxide, manganese dioxide, chromic acid, cericammonium nitrate, bromine, chlorine, and sulfuryl chloride. The oxidation usually takes place in a solvent such as halogenated hydrocarbons, alcohols, ethers, ketones.

The oxidation may also be carried out enzymatically by using an oxidizing enzyme or microbiotically by using a suitable microorganism.

Depending on the process conditions and the starting materials, the compounds of the invention are obtained either in neutral or salt form. Both the neutral compounds and the salts of these are included within the scope of the invention. Thus, basic, neutral or mixed salts may be obtained as well as hemi, mono, sesqui or polyhydrates.

Alkaline salts of the compounds, of the invention are exemplified by their salts with $Li^+$, $Na^+$, $K^+$, $Mg^{2+}$, $Ca^{2+}$, and $N^+(R)_4$, where R is (1–4 C)alkyl. Particularly preferred are the $Na^+$, $Ca^{2+}$ and $Mg^{2+}$ salts. Especially preferred are the $Na^+$ and $Mg^{2+}$ salts. Such salts may be prepared by reacting a compound with a base capable of releasing the desired cation.

Examples of bases capable of releasing such cations, and examples of reaction conditions are given below.

a) Salts wherein the cation is $Li^+$, $Na^+$ or $K^+$ are prepared by treating a compound of the invention with LiOH, NaOH or KOH in an aqueous or nonaqueous medium or with LiOR, LiNH₂, LiNR₂, NaOR, NaNH₂, NaNR₂, KOR, KNH₂ or KNR₂, wherein R is an alkyl group containing 1–4 carbon atoms, in a nonaqueous medium.

b) Salts wherein the cation is $Mg^{2+}$ or $Ca^{2+}$, are prepared by treating a compound of the invention with Mg(OR)₂, Ca(OR)₂ or CaH₂; wherein R is an alkyl group containing 1–4 carbon atoms, in a nonaqueous solvent such as an alcohol (only for the alcoholates), e.g. ROH, or in an ether such as tetrahydrofuran.

Racemates obtained can be separated into the pure enantiomers. This may be done according to known methods, e.g. from racemic diastereomeric salts by means of chromatography or fractional crystallization.

The starting materials described in the intermediate examples may be obtained according to processes known per se.

For clinical use a compound of the invention is formulated into pharmaceutical formulations for oral, rectal, parenteral or other modes of administration. The pharmaceutical formulation contains a compound of the invention normally in combination with a pharmaceutically acceptable carrier. The carrier may be in the form of a solid, semi-solid or liquid diluent, or a capsule. These pharmaceutical preparations are a further object of the invention. Usually the amount of active compound is between 0.1–95% by weight of the preparation, between 0.2–20% by weight in preparations for parenteral use and between 1–50% by weight in preparations for oral administration.

In the preparation of pharmaceutical formulations containing a compound of the present invention in the form of dosage units for oral administration a compound selected may be mixed with a solid, powdered carrier, such as lactose, saccharose, sorbitol, mannitol, starch, amylopectin, cellulose derivatives, gelatin, or another suitable carrier, stabilizing substances such as alkaline compounds e.g. carbonates, hydroxides and oxides of sodium, potassium, calcium, magnesium and the like as well as with lubricating agents such as magnesium stearate, calcium stearate, sodium stearyl fumarate and polyethylenglycol waxes. The mixture is then processed into granules or pressed into tablets. Granules and tablets may be coated with an enteric coating which protects the active compound from acid catalyzed degradation as long as the dosage form remains in the stomach. The enteric coating is chosen among pharmaceutically acceptable enteric-coating materials e.g. beeswax, shellac or anionic film-forming polymers such as cellulose acetate phthalate, hydroxypropyl-methylcellulose phthalate, partly methyl esterified methacrylic acid polymers and the like, if preferred in combination with a suitable plasticizer. To the coating various dyes may be added in order to distinguish among tablets or granules with different active compounds or with different amounts of the active compound present.

Soft gelatine capsules may be prepared with capsules containing a mixture of an active compound of the invention, vegetable oil, fat, or other suitable vehicle for soft gelatine capsules. Soft gelatine capsules may also be enteric-coated as described above. Hard gelatine capsules may contain granules or enteric-coated granules of an active compound. Hard gelatine capsules may also contain an active compound in combination with a solid powdered carrier such as lactose, saccharose, sorbitol, mannitol, potato starch, amylopectin, cellulose derivatives or gelatine. The hard gelatine capsules may be enteric-coated as described above.

Dosage units for rectal administration may be prepared in the form of suppositories which contain an active substance mixed with a neutral fat base, or they may be prepared in the form of a gelatine rectal capsule which contains an active substance in a mixture with a vegetable oil, paraffin oil or other suitable vehicle for gelatine rectal capsules, or they maybe prepared in the form of a ready-made micro enema, or they may be prepared in the form of a dry micro enema formulation to be reconstituted in a suitable solvent just prior to administration.

Liquid preparation for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and/or polyethylene glycol. If desired, such liquid preparations may contain colouring agents, flavouring agents, saccharine and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing agents and/or buffering agents and may be manufactured in different unit dose ampoules or vials. Solutions for parenteral administration may also be prepared as a dry preparation to be reconstituted with a suitable solvent extemporaneously before use.

The typical daily dose of the active substance will depend on various factors such as for example the individual requirement of each patient, the route of administration and the disease. In general, oral and parenteral dosages will be in the range of 5 to 500 mg per day of active substance.

The invention is illustrated by the following examples.

EXAMPLE 1

Preparation of
5-Carbomethoxy-6-methyl-2-[[(4-cyclopropylmethoxy-3-methoxy-2-pyridinyl)methyl]sulfinyl]-1H-benzimidazole 5—Carbomethoxy-6-methyl-2-[[(4-cyclopropylmethoxy-3-methoxy-2-pyridinyl)methyl]thio]]-1H-benzimidazole (0.42 g, 1.0 mmol) was dissolved in methylene chloride (30 ml). NaHCO$_3$ (0.17 g, 2.0 mmol) dissolved in water (5 ml) was added and the mixture was cooled to +2° C. m-chloroperbenzoic acid, 71% (0.19, 0.80 mmol) dissolved in methylene chloride (5 ml) was added dropwise with stirring. Stirring was continued at +2° for 15 min. After separation the organic layer was washed with water, dried with Na$_2$SO$_4$ and evaporated. To the oily residue acetonitrile (1 ml) was added and after cooling the desired product was filtered off as white crystals (0.15 g, 44%).

NMR data are given below.

EXAMPLE 2

Preparation of
5-Acetyl-6-methyl-2-[[(3,4-ethylendioxy-2-pyridinyl)-methyl]sulfinyl]-1H-benzimidazole 5-Acetyl-6-methyl-2-[[(3,4-ethylendioxy-2-pyridinyl)methyl]thio]-1H-benzimidazole (0.17 g, 0.49 mmol) was dissolved in methylene chloride (5 ml). NaHCO$_3$ (0.082 g, 0.97 mmol) dissolved in water (2 ml) was added and the mixture was cooled to +2° C. m-Chloroperbenzoic acid, 69,5% (0.11 g, 0.44 mmol) dissolved in methylene chloride (2 ml) was added dropwise with stirring.

Stirring was continued at +2° C. for 15 min. After separation the organic layer was extracted with an aqueous 0.20M NaOH solution (3×2.5 ml, 1.5 mmol). Methyl formate (0.093 ml, 1.5 mmol) was added to the combined aqueous solutions and after 15 minutes the solution was extracted with methylene chloride. The organic solution was dried over Na$_2$SO$_4$ and evaporated leaving a white crystalline product which was washed with ether. In this way the desired compound was obtained (0.050 g, 30%).

NMR data are given below.

EXAMPLE 3

Preparation of
5-Carbomethoxy-6-methyl-2-[[(3,4-dimethoxy-2-pyridinyl)methyl]sulfinyl]-1H-benzimidazole 5—Carbomethoxy-6-methyl-2-[[(3,4-dimethoxy-2-pyridinyl)methyl]thio]-1H-benzimidazole (1.03 g, 0.00276 mol) was dissolved in $CH_2Cl_2$ (30 ml). $NaHCO_3$ (0.46 g, 0.0055 mol) in $H_2O$ (10 ml) was added and the mixture was cooled to +2° C. m-chloroperbenzoic acid 69.5% (0.62 g, 0.0025 mol) dissolved in $CH_2Cl_2$ (5 ml) was added dropwise under stirring. Stirring was continued at +2° C. for 15 min. After separation the organic layer was extracted with an aqueous 0.2M NaOH solution (3×15 ml, 0.009 mol). After separation the aqueous solutions were combined and neutralized with methyl formate (0.56 ml, 0.009 mol) in the presence of $CH_2Cl_2$ (25 ml). After separation the organic layer was dried over $Na_2SO_4$ and evaporated under reduced pressure. The residue was crystallized from $CH_3CN$ (10 ml) giving the title compound (0.68 g, 70%).

NMR data are given below.

EXAMPLE 4

Preparation of
5-Acetyl-6-methyl-2-[[(3,4-dimethoxy-2-pyridinyl)methyl]sulfinyl]-1H-benzimidazole 5-Acetyl-6-methyl-2-[[(3,4-dimethoxy-2-pyridinyl)methyl]thio]-1H-benzimidazole (3.75 g, 10 mmol) was dissolved in $CH_2Cl_2$ (70 ml). $NaHCO_3$ (1.76 g, 21 mmol) in $H_2O$ (25 ml) was added and the mixture was cooled to $\approx$ +3° C. m-Chloroperbenzoic acid 69.5% (2.43 g, 9.8 mmol) dissolved in $CH_2Cl_2$ (20 ml) was added dropwise under stirring. Stirring was continued for 10 min. The phases were separated and the organic phase was dried over $Na_2SO_4$ and evaporated under reduced pressure. The residue was crystallized from $CH_3CN$ giving the title compound (2.25 g, 60%).

NMR data are given below.

EXAMPLE 5

Preparation of
5-Carbethoxy-2-[[(3,4-dimethoxy-2pyridinyl)methyl]sulfinyl]-1H-benzimidazole 5—Carbethoxy-2-[[(3,4-dimethoxy-2-pyridinyl)methyl]thio]-1H-benzimidazole (95.2% pure) (1.4 g, 0.0036 mol) was dissolved in $CH_2Cl_2$ (30 ml). $NaHCO_3$ (0.6 g, 0.0072 mol in $H_2O$ (10 ml) was added and the mixture was cooled to +2° C. m-Chloroperbenzoic acid 69.5% (0.87 g, 0.0035 mol) dissolved in $CH_2Cl_2$ (5 ml) was added dropwise under stirring. Stirring was continued at +2° C. for 10 min. The phases were separated and the organic phase was dried over $Na_2SO_4$ and evaporated under reduced pressure. The residue was crystallized from $CH_3CN$ (15 ml) giving the title compound (0.76 g, 54%).

NMR data are given below.

EXAMPLE 6

Preparation of
5-Acetyl-6-methyl-2-[[(3,4-propylenedioxy-2-pyridinyl)methyl]]sulfinyl]-1H-benzimidazole The compound was prepared from 5-acetyl-6-methyl-2-[[(3,4-propylenedioxy- 2-pyridinyl)methyl]thio]-1H-benzimidazole and m-chloroperbenzoic acid on a 0.01 mmol scale according to standard procedures.

NMR data are given below.

EXAMPLE 7

5-Acetyl-6-methyl-2-[[(3,4-methylenedioxy-2-pyridinyl)methyl]sulfinyl]-1H-benzimidazole 5-Acetyl-6-methyl-2-[[(3,4-methylenedioxy-2pyridinyl)methyl]thio]-1H-benzimidazole (140 mg, 0,41 mmol) was dissolved in methylene chloride (20 ml) and sodium hydrogen carbonate (5 ml,1M). The mixture was stirred at ambient temperature and MCPBA (100 mg, 0.41 mmol, 70%) dissolved in methylene chloride (10 ml) was added portionwise. After 10 min sodium thiosulphate (100 mg) was added whereupon the phases were separated. The organic phase was dried over sodium sulphate, filtered and concentrated under reduced pressure. The residue was chromatographed on silica ($CH_2Cl_2$/MeOH/$NH_3$, 97.5: 2.5: sat.) Yield: 90 mg (61%) of the title compound. Mp: 178°–180° C. (dec., uncorr.).

NMR data are given below.

EXAMPLE 8

Preparation of
5-Acetyl-6-methyl-2-[[(3-methoxy-4-(5-methyl-1,3-dioxan-5-yl-methoxy)-2-pyridinyl)methyl]-sulfinyl]-1H-benzimidazole A stirred mixture of 5-acetyl-6-methyl-2-[[(3-methoxy-4-(5-methyl-1,3-dioxan-5-yl-methoxy)-2-pyridinyl)methyl]thio]-1H-benzimidazole (87 mg, 0.19 mmol) in 20 ml $CH_2Cl_2$ and $NaHCO_3$(32 mg, 0.38 mmol) in 5 ml $H_2O$ was cooled to 0° C. and treated with 3-chloro-perbenzoic acid (47 mg 70%, 0.19 mmol). After reacting for 10 min the layers were separated (the aqueous layer was washed once more with 5 ml $CH_2Cl_2$) and the organic layer extracted with 10 ml $H_2O$ containing NaOH (15 mg, 38 mmol). The alkaline aqueous layer was collected and treated with several portions of methyl formate (each 23 µl, 38 mmol) until the solution turned opaque. The aqueous layer was extracted with 25+10 ml $CH_2Cl_2$. The two latter organic layers were combined, dried over $MgSO_4$ and evaporated. The residue was chromatographed ($SiO_2$, $CH_2Cl_2$/MeOH saturated with $NH_{3(g)}$, 93/7) yielding 40 mg (44%) pure solfoxide.

NMR data are given below.

EXAMPLE 9

Preparation of
5-acetyl-6-methyl-[[(3,4-dimethoxy-2-pyridinyl)methyl]sulfinyl]-1H-benzimidazole, Sodium Salt 5-Acetyl-6-methyl-2-[[(3,4-dimethoxy-2-pyridinyl)methyl]sulfinyl]-1H-benzimidazole (0.50 g, 1.3 mmol) dissolved in dichloromethane and sodium hydroxide (51 mg, 1.3 mmol) dissolved in water (6 ml) were transferred to a seporatory funnel. The mixture was shaken to equilibrium whereupon the solvent phases were separated. The aqueous solution was washed with dichloromethane and then freeze dried.

NMR data are given below.

EXAMPLE 10

Preparation of
5-acetyl-6-methyl-2-[[(4cyclopropylmethoxy-3-methoxy-2-pyridinyl)methyl]sulfinyl]-1H-benzimidazole 5-Acetyl-6-methyl-2-[[(4-cyclopropylmethoxy-3-methoxy-2-pyridinyl)methyl]thio]-1H-benzimidazole (40 mg, 0.10 mmol) was dissolved in methylene chloride (10 ml) and sodium hydrogen carbonate (3 ml,1M). The mixture was stirred at ambient temperature and MCPBA (25 mg, 0.10 mmol, 70%) dissolved in methylene chloride (5 ml) was added portionwise. After 10 min sodium thiosulphate (30 mg) was added whereupon the phases were separated. The organic phase was dried over sodium sulphate, filtered and concentrated under reduced pressure. The residue was chromatographed on silica ($CH_2Cl_2$/MeOH/$NH_3$, 97.5:2.5:sat.) Yield 30 mg (73%) of the title compound.

TABLE 1

| Ex | Solvent | NMR data δ ppm |
|---|---|---|
| 1 | $CDCl_3$ (300 MHz) | 0.30–0.35(m, 2H), 0.60–067(m, 2H), 1.2–1.3(m, 1H) 2.67(s, 3H), 3.83(d, 2H), 3.86(s, 3H), 3.90(s, 3H), 4.72(d, 1H), 4.86(d, 1H), 6.71(d, 1H), 7.35(b, 1H), 8.09(d, 1H), 8.24(b, 1H), |
| 2 | $CDCl_3$ (500 MHz) | 2.65(s, 3H), 2.66(s, 3H), 3.9–4.2(m, 4H), 4.70(d, 1H), 4.82(d, 1H), 6.75(d, 1H), 7.3(b, 1H), 7.92(d, 1H), 8.2(b, 1H), |
| 3 | $CDCl_3$ (500 MHz) | 2.70(s, 3H), 3.85(s, 3H), 3.90(s, 3H), 3.95(s, 3H), 4.70(d, 1H), 4.90(d, 1H), 6.8(d, 1H), 7.30(b, 1H), 8.20(d, 1H), 8.35(b, 1H). |
| 4 | $CDCl_3$ (300 MHz) | 2.60(s, 6H), 3.85(s, 3H), 3.85(s, 3H), 4.70(d, 1H), 4.90(d, 1H), 6.80(d, 1H), 7.30(b, 1H), 8.15(d, 1H), 8.20(b, 1H) |
| 5 | $CDCl_3$ (300 MHz) | 1.45(t, 3H), 3.85(s, 3H), 3.90(s, 3H), 4.40(q, 2H), 4.65(d, 1H), 4.40(d, 1H), 6.80(d, 1H), 7.50 7.80(b, 1H) 8.05(d, 1H), 8.20(d, 1H), 8.25, 8.55(b, 1H) |
| 6 | $CDCl_3$ (500 MHz) | 2.16(m, 2H), 2.64(s, 3H), 2.66(s, 3H), 4.23(t, 2H), 4.30(t, 2H), 4.68(d, 1H), 4.88(d, 1H), 6.83(d, 1H), 7.3–7.5(b, 1H), 8.01(d, 1H), 8.1–8.2(b, 1H). |
| 7 | $CDCl_3$ (300 MHz) | 2.66(s, 6H), 4.54(d, 1H), 4.75(d, 1H), 5.80(s, 1H), 5.87(s, 1H), 6.77(d, 1H), 7.93(br, 1H), 8.07(d, 1H), 8.12(br, 1H) |
| 8 | $CDCl_3$ (300 MHz) | 0.91(s, 3H), 2.63(s, 3H), 2.64(s, 3H), 3.49(d, 2H), 3.84(s, 3H), 3.94(d, 2H), 4.15(m, 2H), 4.66(d, 1H), 4.73(d, 1H), 4.86(d, 1H), 5.02(d, 1H), 6.89(d, 1H), 7.33(s, 1H), 8.08(s, 1H), 8.14(d, 1H) |
| 9 | $D_2O$ (protons in water were set to 4.82 ppm) (300 MHz) | 2.66(s, 3H), 2.81(s, 3H), 3.81(s, 3H), 4.02(s, 3H), 4.73(d, 1H), 4.91(d, 1H), 7.16(d, 1H), 7.62(s, 1H), 8.23(d, 1H), 8.30(s, 1H) |
| 10 | $CDCl_3$ (300 MHz) | 0.33(m, 2H), 0.65(m, 2H), 1.24(m, 1H), 2.63(s, 3H), 2.64(s, 3H), 3.84(d, 2H), 3.88(s, 3H), 4.73(d, 1H), |

TABLE 1-continued

| Ex | Solvent | NMR data δ ppm |
|---|---|---|
| | | 4.83(d, 1H), 6.73(d, 1H), 7.35(s, 1H), 8.08(s, 1H), 8.11(d, 1H) |

EXAMPLE OF INTERMEDIATES

EXAMPLE I 1

Preparation of
5-Carbomethoxy-6-methyl-2-[[(4-cyclopropylmethoxy-3-methoxy-2-pyridinyl)methyl]thio]-1H-benzimidazole To a solution of 5-carbomethoxy-6-methyl-2-mercapto-1H-benzimidazole (0.58 g, 2.6 mmol) in methanol (25 ml) aqueous NaOH (1.0 ml 5M, 5.0 mmol) and 4-cyclopropylmethoxy-3-methoxy-2-chloromethyl pyridine hydrochloride (prepared according to processes known per se.) (0.63 g, 2.4 mmol) dissolved in methanol (25 ml were added in the given order. The mixture was refluxed for one hour whereupon the solution was evaporated. The residue was partitioned between methylene chloride and water. After separation the organic solution was dried over $Na_2SO_4$ and evaporated giving a yellow syrup (1.0 g, 100%).

NMR data are given below.

EXAMPLE I 2

5-Acetyl-6-methyl-2-[[(3,4-ethylendioxy-2-pyridinyl)-methyl]thio]-1H-benzimidazole To a solution of 5-acetyl-6-methyl-2-mercapto-1H-benzimidazole (0.14 g, 0.66 mmol) in methanol (2 ml) aqueous NaOH (0.25 ml 5M, 1.25 mmol) and 3,4-ethylendioxy-2-chloromethyl pyridine hydrochloride (0.13 g, 0.60 mmol) dissolved in methanol (2 ml) were added in the given order. The mixture was refluxed for one hour whereupon the solution was evaporated. The residue was partitioned between methylene chloride and water. After separation the organic solution was dried over $Na_2SO_4$ and evaporated giving a yellow syrup (0.17 g, 81%).

NMR data are given below.

EXAMPLE I 3

Preparation of
5-Carbomethoxy-6-methyl-2-[[(3,4-dimethoxy-2-pyridinyl)methyl]thio]-1H-benzimidazole 5-Carbomethoxy-6-methyl-2-mercapto-1H-benzimidazole (0.67 g, 0.003 mol) and NaOH (0.12g, 0.003 mol) in $H_2O$ (0.6 ml) were dissolved in $CH_3OH$ (15 ml). 3,4-dimethoxy-2-chloromethylpyridine hydrochloride, (=0.0036 mol) as a crude material in $CH_3OH$ (10 ml) and NaOH (0.144 g, 0.0036 mol) in $H_2O$ (0.72 ml) were added. The mixture was heated to reflux and the reflux was continued for 1 hour. $CH_3OH$ was evaporated off and the crude material was purified by chromatography on a silica column using $CH_2Cl_2$—$CH_3OH$ (98–2) as eluent, giving (1.03 g, 92%) of the pure title compound.

NMR data are given below.

EXAMPLE I 4

Preparation of
5-acetyl-6-methyl-2-[[(3,4-dimethoxy-2-pyridinyl)methyl]thio]-1H-benzimidazole 5-Acetyl-6-methyl-2-mercapto-1H-benzimidazole (4.2 g, 20 mmol) and NaOH (0.8 g, 20 mmol) in $H_2O$ (1 ml) were dissolved in 60 ml ethanol. 3,4-dimethoxy-2-chloromethylpyridine hydrochloride ($\approx 17$ mmol) as a crude material was added and the mixture was heated to boiling. NaOH (0.7 g, 17 mmol) in $H_2O$ (1 ml) was added and the reflux was continued for 6 hours. The solvent was evaporated off and the residue was diluted with methylene chloride and water. The organic phase was dried over $Na_2SO_4$ and the solvent was removed under reduced pressure. Crystallizing from acetonitrile gave the title compound, (3.75 g, 62%).

NMR data are given below.

EXAMPLE I 5

Preparation of
5-Carbethoxy-2-[[(3,4-dimethoxy-2-pyridinyl)methyl]-thio]-1H-benzimidazole 5-Carbethoxy-2-mercapto-1H-benzimidazole (2.0 g, 9 mmol) and NaOH (0.36 g, 9 mmol) in $H_2O$ (1 ml) were dissolved in ethanol (30 ml). 3,4-dimethoxy-2-chloromethylpyridine hydrochloride ($\approx 6.6$ mmol) as a crude material were added and the mixture was heated to boiling. NaOH (0.26 g, 6.6 mmol) in $H_2O$ (1 ml) was added and the reflux was continued for 6 hours. The solvent was evaporated off and the residue was diluted with methylene chloride and water. The organic phase was dried over $Na_2SO_4$ and the solvent removed under reduced pressure. Crystallizing from $CH_3CN$ gave the desired product (1.75 g, 71%).

NMR data are given below.

EXAMPLE I 6

Preparation of
5-acetyl-6-methyl-2-[[(3,4-propylenedioxy-2-pyridinyl)-methyl]thio]-1H-benzimidazole The compound was prepared from 5-acetyl-2-mercapto-6-methyl-1H-benzimidazole and 2-chloromethyl-3,4-propylenedixoxypyridine on a 0.01 mmol scale according to standard procudures.

NMR data are given below.

EXAMPLE I 7

Preparation of
5-acetyl-6-methyl-2-[[(3,4-methylenedioxy-2-pyridinyl)methyl]thio]-1H-benzimidazole 2-Chloromethyl-3,4-methylenedioxypyridine (90 mg, 0.52 mmol) and 5-acetyl-6-methyl-2-mercaptobenzimidazole (214 mg, 1.04 mmol) were dissolved in ethanol (15 ml). The pH value of the solution was adjusted to 9 (0.2M NaOH) whereupon the solution was refluxed for 10 min. After concentration of the reaction mixture at reduced pressure the residue was taken up in methylene chloride (10 ml) and brine (2 ml). The phases were separated and the organic phase was dried over sodium sulphate, filtered and concentrated at reduced pressure. The residue was chromatographed on silica (ethyl acetate). Yield: 140 mg (79%) of the title compound. Mp: 141°–143° C. (uncorr.)

NMR data are given below.

EXAMPLE I 8

Preparation of
5-acetyl-6-methyl-2-[[(3-methoxy-4-(5-methyl-1,3-dioxan-5-yl-methoxy)-2-pyridinyl)methyl]-thio]-1H-benzimidazole A solution of 2-(hydroxymethyl)-3-methoxy-4-(5-methyl-1,3-dioxan-5-yl-methoxy)pyridine (0.34 g, 1.3 mmol) in 10 ml $CH_2Cl_2$ was cooled to 0° C. and treated with $SOCl_2$ (0.12 ml, 1.7 mmol). The solution was allowed to warm to room temperature and reacted for 1 h. Evaporation of the solvent furnished a quantitative yield of the corresponding chloromethyl derivative as the hydrochloride. DI-MS, m/z (%): 289 and 287 (11 and 38). A suspension of 5-acetyl-2-mercapto-6-methyl-1H-benzimidazole (0.29 g, 1.4 mmol) in 10 ml MeOH was treated with a solution of NaOH (0.10 g, 2.6 mmol) in 1.5 ml $H_2O$. The formed solution was treated with the prepared chloromethyl compound and reacted for 21 h at room temperature. The solvent was evaporated and the residue taken up in 20 ml 2.5% NaOH. The aqueous layer was extracted with 50+25 ml $CH_2Cl_2$, the organic layers combined, dried over $MgSO_4$, and evaporated leaving 0.49 g (82%) title compound as a tanned foam.

NMR data are given below.

EXAMPLE I 9

Preparation of
5-acetyl-6-methyl-2-[[(4-cyclopropylmethoxy-3-methoxy-2-pyridinyl)methyl]thio]- 1H-benzimidazole 2-Chloromethyl-4-cyclopropylmethoxy-3-methoxypyridine (50 mg, 0.22 mmol) and 5-acetyl-6-methyl-2-mercaptobenzimidazole (50 mg, 0.24 mmol) were dissolved in ethanol (15 ml). The pH value of the solution was adjusted to 9 (0.2M NaOH) whereupon the solution was refluxed for 10 min. After concentration of the reaction mixture at reduced pressure the residue was taken up in methylene chloride (10 ml) and brine (2 ml). The phases were separated and the organic phase was dried over sodium sulphate, filtered and concentrated at reduced pressure. The residue was chromatographed on silica (ethyl acetate). Yield: 40 mg (46%) of the title compound.

NMR data are given below.

EXAMPLE I 10

Preparation of
4-Chloro-3-hydroxyethoxy-2-methylpyridine

A solution of 4-chloro-3-methoxyethoxy-2-methylpyridine (2.78 g, 0.014 mol) in dry $CDCl_3$ ($\approx 14$ ml) under Ar was treated with TMSI (5.10 ml, 0.036 mol) for 23 h at room temperature. The reaction mixture was partitioned between 100 ml $CH_2Cl_2$ and 100 ml 1M HCl. The aqueous layer was collected, washed once more with 50 ml $CH_2Cl_2$, and then treated with $Na_2CO_3$ until the pH was $\approx 10$. The aqueous layer was extracted with 100+50 ml $CH_2Cl_2$. The two latter organic layers were combined, dried over $MgSO_4$ and evaporated leaving 2.31 g enriched product.

Chromatography (silica gel, diethyl ether followed by diethyl ether/MeOH;95/5) afforded 1.06 g (40%) pure product.

NMR data are given below.

EXAMPLE I 11

Preparation of 3,4-Ethylenedioxy-2-methylpyridine

A mixture of 4-chloro-3-hydroxyethoxy-2-methylpyridine (1.03g, 0.0055 mol) and NaH (55% in oil, 599 mg, 0.0138 mol) in 600 ml THF was refluxed for 15 h. Excess NaH was destroyed with 3 ml of $H_2O$. The solvent was evaporated and the residue partitioned between 100 ml 1M HCl and 100 ml $CH_2Cl_2$. The aqueous layer was collected, washed once more with 100 ml $CH_2Cl_2$ and then treated with $Na_2CO_3$ until the pH was ≈10. The aqueous layer was extracted with 150+100 ml CH₂Cl₂. The two latter organic layers were combined, dried over MgSO₄, and evaporated leaving 720 mg enriched product. Chromatography (silica gel, diethyl ether) furnished 0.49 g (59%) pure product.

NMR data are given below.

EXAMPLE I 12

Preparation of 3,4-Ethylenedioxy-2-hydroxymethyl-pyridine

The title compound was prepared on a 3.2 mmol scale according to standard procedures yielding 395 mg (77%) pure product.

NMR data for the intermediate are given below.

EXAMPLE I 13

Preparation of 3-(3-Hydroxy-1-propoxy)-2-methyl-4-pyrone

A suspension of 3-hydroxy-2-methyl-4-pyrone (25 g, 200 mmol), 3-bromo-1-propanol (70 g, 500 mmol) and K₂CO₃ (111 g 800 mmol) in 600 ml acetone was stirred for three days. The solvent was evaporated and the residue partitioned between 300 ml methylene chloride and 500 ml 2.5% NaOH. The aqueous layer was separated and extracted with 2×300 ml methylene chloride. The organic phases were combined, dried over Na₂SO₄ and evaporated at 50° C. Eight grams of the residue (24 g) was chromatographed on silica gel with methanol/methylene chloride (5:95) as eluent which afforded 2.7 g (22%) of the desired product as an oil.

NMR data are given below.

EXAMPLE I 14

Preparation of 3-(3-methoxy-1-propoxy)-2-methyl-4-pyrone

A mixture of 3-(3-hydroxy-1-propoxy)-2-methyl-4-pyrone (1.4 g, 7.6 mmol), 85% KOH (0.55 g, 8.4 mmol) and methyliodide (11 g, 76 mmol) was stirred at room temperature for one day. The red solution was partitioned between methylene chloride and half saturated aqueous ammoniumchloride solution. The organic phase was washed with water, dried over Na₂SO₄ and evaporated. The residue was purified by chromatography on silica gel with methanol/methylene chloride (3:97) as eluent. Removing the eluent by film evaporation afforded 0.31 g (20%) of the desired product as an oil.

NMR data are given below.

EXAMPLE I 15

Preparation of 3-(3-methoxy-1-propoxy)-2-methyl-4-pyridone

A solution of 3-(3-methoxy-1-propoxy)-2-methyl-4-pyrone (0.31 g, 1.7 mmol) in 50 ml concentrated aqueous NH₃ was heated to 120° C. for 2 h in an autoclave. The reaction mixture was transferred to a round bottomed flask and evaporation off the solvent afforded 0.32 g (100%) product as a yellow oil.

NMR data are given below.

EXAMPLE I 16

Preparation of 4-chloro-3-(3-methoxy-1-propoxy)-2-methylpyridine

A solution of 3-(3-methoxy-1-propoxy)-2-methyl-4-pyridone (0.32 g, 1.6 mmol) in 50 ml POCl₃ was refluxed for 14 h. The POCl₃ was evaporated off and the residue was partitioned between methylene chloride and water. The aqueous layer was separated, treated with K₂CO₃ until pH=10 and extracted with methylene chloride. The organic layer was dried over Na₂SO₄ and evaporated. The residue was purified by chromatography on silica gel with methanol/methylene chloride (3:97) as eluent. Evaporation off the solvent afforded 0.12 g (34%) product as a red oil.

NMR data are given below.

EXAMPLE I 17

Preparation of 4-chloro-3-(3-hydroxy-1-propoxy)-2-methylpyridine

To a solution of 4-chloro-3-(3-methoxy-1-propoxy)-2-methylpyridine (120 mg, 0.56 mmol) in 2 ml of CDCl₃ was added trimethylsilyl iodide (0.16 ml, 1.3 mmol), this was done in a NMR tube. The reaction was complete after four days as indicated by the absence of a signal for the OCH₃ protons at 3.3 ppm in the NMR spectrum. The solution was poured over 10 ml of 1M HCl whereupon the mixture was stirred for 5 minutes with 10 ml of methylene chloride. The aqueous layer was separated, treated with K₂CO₃ until pH=10 and extracted with methylene chloride. The organic phase was dried over Na₂SO₄ and evaporated. This afforded 0.049 g (43%) of the desired product as a yellow oily film.

NMR data are given below.

EXAMPLE I 18

Preparation of 2-methyl-3,4-propylenedioxy-pyridine

A solution of 4-chloro-3-(3-hydroxy-1-propoxy)-2-methylpyridine (49 mg, 0.24 mmol) in 3 ml of DMSO was heated for 2 h at 70° C. with 55% NaH (32 mg, 0.73 mmol). The mixture was cooled, diluted with water and extracted with methylene chloride. The organic solution was evaporated and the residue was chromatographed on silica gel with methylene chloride as eluent. The solvent was evaporated which afforded 22 mg (55%) of a yellow oil.

NMR data are given below.

EXAMPLE I 19

Preparation of 2-Hydroxymethyl-3,4-propylene-dioxypyridine

The title compound was prepared from 2-methyl-3,4-propylenedioxypyridine on a 0.01 mmol scale according to standard procedures yielding 3 mg (11%) product.

NMR data are given below.

EXAMPLE I 20

Preparation of 2-Chloromethyl-3,4-propylene-dioxypyridine

The title compound was prepared from 2-hydroxymethyl-3,4-propylenedioxypyridine in a quantitative yield on a 0.01 mmol scale according to standard procedures. The compound was used in the synthesis without purification and characterisation.

EXAMPLE I 21

Preparation of 2-Methyl-3,4-methylenedioxypyridine

2-Methyl-3-hydroxy-4-pyridone (1.25 g, 10 mmol) was dissolved in dry DMSO (20 ml). Dibromomethane (3.5 g, 20 mmol) was added followed by sodium hydride (1 g, >20 mmol, 50–60% in oil). The mixture was left at ambient temperature under stirring for 3 days whereupon it was poured into brine (50 ml). The water-

EXAMPLE I 22

Preparation of
2-Methyl-3,4-methylenedioxypyridine-N-oxide

To the methylene chloride solution of 2-methyl-3,4-methylenedioxypyridine from example I 21 sodium hydrogen carbonate (1M, 50 ml) and MCPBA (4 g, 70%) were added. The mixture was stirred at ambient temperature for 15 min whereupon the excess of MCPBA was destroyed with addition of sodium thiosulphate (1 g). The organic phase was separated and the aqueous phase was extracted with methylene chloride (3×50 ml). The collected organic phases were concentrated under reduced pressure and chromatographed on silica ($CH_2Cl_2$/MeOH, 90:10). Yield: 120 mg (7,8%) of the title compound.

NMR data are given below.

EXAMPLE I 23

Preparation of
2-Hydroxymethyl-3,4-methylenedioxypyridine

2-Methyl-3,4-methylenedioxypyridine-N-oxide (120 mg, 0.78 mmol) was dissolved in acetic anhydride (10 ml) and the solution was heated at 110° C. for 15 min, whereupon the mixture was concentrated under reduced pressure. The residue was dissolved in methanol (20 ml) and sodium hydroxide (3 drops, 6M) was added. After 30 min at ambient temperature the mixture was neutralised with acetic acid (pH 6) and concentrated under reduced pressure. The residue was chromatographed on silica (hexane/ethyl acetate, 1:1). Yield: 90 mg (75%) of the title compound.

NMR data are given below.

EXAMPLE I 24

Preparation of
2-chloromethyl-3,4-methylenedioxypyridine

2-Hydroxymethyl-3,4-methylenedioxypyridine (90 mg, 0.59 mmol) was dissolved in methylene chloride (10 ml) and thionyl chloride (240 mg, 2 mmol) was added. After 10 min at ambient temperature the mixture was hydrolysed with sodium hydrogen carbonate and the phases were separated. The organic phase was dried over sodium sulphate, filtered and concentrated under reduced pressure. Yield: 90 mg (88%) of the title compound (crude).

NMR data are given below.

EXAMPLE I 25

Preparation of
3-Methoxy-2-methyl-4-(5-methyl-1,3-dioxan-5-yl-methoxy)pyridine-N-oxide A deareated solution of 5-(hydroxymethyl)-5-methyl-1,3-dioxane (1.19 g, 9 mmol) in 125 ml dry THF was treated with NaH (0.79 g 55% dispersion in oil, 18 mmol) for 20 min. 4-Chloro-3-methoxy-2-methylpyridine-N-oxide (1.04 g, 6 mmol) was added and the mixture was refluxed for 26 h. Excess NaH was quenched with 10 ml of $H_2O$ and the solvent evaporated. The residue was partitioned between 150 ml $CH_2Cl_2$ and 50 ml 5% $Na_2CO_3$. The organic layer was passed through a phase separation paper and evaporated leaving 1.83 g enriched product. Chromatography ($SiO_2CH_2Cl_2$/MeOH, 95/5) afforded 0.39 g (24%) pure title compound as a tanned oil.

NMR data are given below.

EXAMPLE I 26

Preparation of
2-(hydroxymethyl)-3-methoxy-4-(5-methyl-1,3-dioxan-5-yl-methoxy)pyridine A solution of 3-methoxy-2-methyl-4-(5-methyl-1,3-dioxan-5-yl-methoxy)pyridine-N-oxide (0.39 g, 1.5 mmol) in 4.5 ml $(CH_3CO)_2O$ was heated to 100° C. for 4 h. Excess $(CH_3CO)_2O$ was azeotroped off 4 times with 75 ml portions of abs. EtOH leaving 0.42 g (90%) crude 3-methoxy-4-(5-methyl-1,3-dioxan-5-yl-methoxy)-2-pyridinyl)-methyl acetate.

The crude acetate was treated with 20 ml 2M NaOH for 1 h at 100° C. The aqueous layer was extracted with 75+50 +25 ml $CH_2Cl_2$. The organic layers were combined, dried over $MgSO_4$, and evaporated leaving 0.34 g (97%) product pure enough for further use.

NMR data are given below.

TABLE 2

| Ex | Solvent | NMR data δ ppm |
|---|---|---|
| I 1 | CDCl$_3$ (300 MHz) | 0.37–0.42(m, 2H), 0.67–0.73(m, 2H), 1.25–1.40(m, 1H) 2.69(s, 3H), 3.90(s, 3H), 3.94(d, 2H), 3.98(s, 3H), 4.40(s, 2H) 6.81(d, 1H), 7.3(b, 1H), 8.2(b, 1H), 8.22(d, 1H), |
| I 2 | CDCl$_3$ (500 MHz) | 2.64(s, 3H), 2.66(s, 3H), 4.35(s, 2H), 4.40(s, 4H), 6.85(d, 1H), 7.30(s, 1H), 8.06(d, 1H), 8.08(s, 1H). |
| I 3 | CDCl$_3$ (300 MHz) | 2.70(s, 3H), 3.90(s, 3H), 3.95(s, 3H), 4.00(s, 3H), 4.40(s, 2H), 6.90(d, 1H), 7.35(s, 1H), 8.20(s, 1H), 8.25(d, 1H) |
| I 4 | CDCl$_3$ (300 MHz) | 2.60(s, 3H), 2.65(s, 3H), 3.90(s, 3H), 3.90(s, 3H), 4.35(s, 2H), 6.85(d, 1H), 7.25(s, 0.6H), 7.40(s, 0.4H), 7.85(s, 0.4H), 8.05(s, 0.6H), 8.30(m, 1H) |
| I 5 | CDCl$_3$ (300 MHz) | 1.40(m, 3H), 3.90(s, 3H), 3.90(s, 3H), 4.40(m, 4H), 6.90(dd, 1H), 7.45(d, 0.4H), 7.60(d, 0.6H), 7.90(m, 1H), 8.20(s, 0.6H), 8.25(m, 1H), 8.25(s, 0.4H) |
| I 6 | CDCl$_3$ (500 MHz) | 2.32(p, 2H), 2.64(s, 3H), 2.66(s, 3H), 4.37–4.43(m, 4H), 4.39(s, 2H), 6.88–6.90(m, 1H), 7.29(s, 0.6H), 7.42(s, 0.4H), 7.85(s, 0.4H), 8.07(s, 0.6H), 8.11(m, 1H) |
| I 7 | CDCl$_3$ (300 MHz) | 2.648(s, 3H), 2.652(s, 3H), 4.32(s, 2H), 6.14(s, 2H), 6.85(d, 1H), 7.34(br, 1H), 8.00(br, 1H), 8.20(d, 1H) |
| I 8 | CDCl$_3$ (300 MHz) | 0.98(s, 3H), 2.65(coinciding s, 6H), 3.53(d, 2H), 3.95(s, 3H), 4.00(d, 2H), 4.25(s, 2H), 4.39(s, 2H), 4.69(m, 1H), 5.06(m, 1H), 6.9–7.0(2d, 1H), 7.3–7.5(several b, 1H), 7.8–8.1(several b, 1H), 8.2–8.3(2d, 1H), 13.2(b, 1H) |
| I 9 | CDCl$_3$ (300 MHz) | 0.38(m, 2H), 0.69(m, 2H), 1.31(m, 1H), 2.63(s, 3H), 2.636(s, 3H), 3.93(d, 2H), 3.98(s, 3H), 4.40(s, 2H), 6.81(d, 1H), 7.33(s, 1H), 7.98(s, 1H), 8.22(d, 1H) |
| I 10 | CDCl$_3$ (500 MHz) | 2.57(s, 3H), 2.70(t, 1H) 3.99(dt, 2H), 4.09(t, 2H), |

TABLE 2-continued

| Ex | Solvent | NMR data δ ppm |
|---|---|---|
| I 11 | CDCl$_3$ (500 MHz) | 7.19(d, 1H), 8.16(d, 1H) 2.41(s, 3H), 4.30(s, 4B), 6.65(d, 1H), 7.90(d, 1H), |
| I 12 | CDCl$_3$ (500 MHz) | 4.11(b, 1H), 4.33(m, 4H), 4.69(b, 2H), 6.76(d, 1H), 7.99(d, 1H) |
| I 13 | CDCl$_3$ (300 MHz) | 1.85(p, 2H), 2.30(s, 3H), 3.85(q, 2H), 4.00(t, 2H), 4.35(t, 1H), 6.35(d, 1H), 7.65(d, 1H) |
| I 14 | CDCl$_3$ (300 MHz) | 2.00(p, 2H), 2.32(s, 3H), 3.35(s, 3H), 3.56(t, 2H), 4.13(t, 2H), 6.33(d, 1H), 7.59(d, 1H) |
| I 15 | CDCl$_3$ (300 MHz) | 1.98(p, 2H), 2.45(s, 3H), 3.38(s, 3H), 3.61(t, 2H), 4.08(t, 2H), 6.53(d, 1H), 7.63(d, 1H) |
| I 16 | CDCl$_3$ (300 MHz) | 2.09(p, 2H), 2.54(s, 3H), 3.38(s, 3H), 3.63(t, 2H), 4.04(t, 2H), 7.16(d, 1H), 8.13(d, 1H) |
| I 17 | CDCl$_3$ (500 MHz) | 2.10(p, 2H), 2.56(s, 3H), 3.96(t, 2H), 4.10(t, 2H), 7.18(d, 1H), 8.15(d, 1H) |
| I 18 | CDCl$_3$ (300 MHz) | 2.25(p, 2H), 2.45(s, 3H), 4.28(t, 2H), 4.34(t, 2H), 6.70(d, 1H), 7.96(d, 1H) |
| I 19 | CDCl$_3$ (500 MHz) | 2.27(p, 2H), 4.30(t, 2H), 4.37(t, 2H), 4.71(d, 2H), 6.80(d, 2H), 8.05(d, 1H) |
| I 21 | CDCl$_3$ (500 MHz) | 2.34(s, 3H), 5.92(s, 2H), 6.61(d, 1H), 7.93(d, 1H) |
| I 22 | CDCl$_3$ (500 MHz) | 2.42(s, 3H), 6.12(s, 2H), 6.59(d, 1H), 7.90(d, 1H) |
| I 23 | CDCl$_3$ (300 MHz) | 4.73(s, 2H), 6.05(s, 2H), 6.76(d, 1H), 8.09(d, 1H) |
| I 24 | CDCl$_3$ (300 MHz) | 4.65(s, 2H), 6.10(s, 2H), 6.78(d, 1H), 8.13(d, 1H) |
| I 25 | CDCl$_3$ (300 MHz) | 0.97(s, 3H), 2.50(s, 3H), 3.52(d, 2H), 3.85(s, 3H), 3.98(d, 2H), 4.18(s, 2H), 4.67(d, 1H), 5.02(d, 1H), 6.77(d, 1H), 8.08(d, 1H) |
| I 26 | CDCl$_3$ (300 MHz) | 0.98(s, 3H), 3.52(d, 2H), 3.86(s, 3H), 4.00(d, 2H), 4.09(m, 1H), 4.20(s, 2H), 4.68(d, 1H), 4.75(d, 2H), 5.02(d, 1H), 6.88(d, 1H), 8.20(d, 1H) |

The best mode of carrying out the invention known at present is to use the compound according to Example 4 or its salt according to Example 9.

TABLE 3

Examples of compounds included in the formula I are given in the following table

| Ex. | R$^1$ | R$^2$ | R$^3$ | R$^4$ | Yield % | Ident. data |
|---|---|---|---|---|---|---|
| 1 | C(O)—OCH$_3$ | CH$_3$ | CH$_3$ | CH$_2$ | 44 | NMR |
| 2 | C(O)CH$_3$ | CH$_3$ | —CH$_2$CH$_2$— | | 30 | NMR |
| 3 | C(O)—OCH$_3$ | CH$_3$ | CH$_3$ | CH$_3$ | 70 | NMR |
| 4 | C(O)CH$_3$ | CH$_3$ | CH$_3$ | CH$_3$ | 60 | NMR |
| 5 | C(O)OCH$_2$CH$_3$ | H | CH$_3$ | CH$_3$ | 54 | NMR |
| 6 | C(O)CH$_3$ | CH$_3$ | —CH$_2$CH$_2$CH$_2$— | | | NMR |
| 7 | C(O)CH$_3$ | CH$_3$ | —CH$_2$— | | 61 | NMR |
| 8 | C(O)CH$_3$ | CH$_3$ | CH$_3$ | CH$_2$ | 44 | NMR |
| 9 | C(O)CH$_3$ | CH$_3$ | CH$_3$ | CH$_3$ | sodium salt | NMR |
| 10. | C(O)CH$_3$ | CH$_3$ | CH$_3$ | CH$_2$ | 73 | NMR |

Syrup

A syrup containing 1% (weight per volume) of active substance was prepared from the following ingredients:

| Compound according to Example 4 | 1.0 g |
|---|---|
| Sugar, powder | 30.0 g |
| Saccharine | 0.6 g |
| Glycerol | 15.0 g |
| Flavouring agent | 0.05 g |
| Ethanol 96% | 5.0 g |
| Distilled water q.s. to a final volume of | 100 ml |

Sugar and saccharine were dissolved in 60 g of warm water. After cooling the active compound was added to the sugar solution and glycerol and a solution of flavouring agents dissolved in ethanol were added. The mixture was diluted with water to a final volume of 100 ml.

Enteric-coated Tablets

An enteric coated tablet containing 50 mg of active compound was prepared from the following ingredients:

| Compound according to Example 4 as Mg salt | 500 g |
|---|---|
| Lactose | 700 g |
| Methyl cellulose | 6 g |
| Polyvinylpyrrolidone cross-linked | 50 g |
| Magnesium stearate15 g Sodium carbonate | 6 g |
| Distilled water | q.s. |
| Cellulose acetate phthalate | 200 g |
| Cetyl alcohol | 15 g |
| Isopropanol | 2000 g |
| Methylene chloride | 2000 g |

I

Compound according to example 1, powder, was mixed with lactose and granulated with a water solution of methyl cellulose and sodium carbonate. The wet mass was forced through a sieve and the granulate dried in an oven. After drying the granulate was mixed with polyvinylpyrrolidone and magnesium stearate. The dry mixture was pressed into tablet cores (10 000 tablets), each tablet containing 50 mg of active substance, in a tabletting machine using 7 mm diameter punches.

II

A solution of cellulose acetate phthalate and cetyl alcohol in isopropanol/methylene chloride was sprayed onto the tablets I in an Accela Cota$^R$, Manesty coating equipment. A final tablet weight of 110 mg was obtained.

Solution for Intravenous Administration

A parenteral formulation for intravenous use, containing 4 mg of active compound per ml, was prepared from the following ingredients:

| Compound according to Example 9 | 4 g |
|---|---|
| Sterile water to a final volume of | 1000 ml |

The active compound was dissolved in water to a final volume of 1000 ml. The solution was filtered through a 0.22 μm filter and immediately dispensed into 10 ml sterile ampoules. The ampoules were sealed.

Capsules

Capsules containing 30 mg of active compound were prepared from the following ingredients:

| | |
|---|---|
| Compound according to Example 4 | 300 g |
| Lactose | 700 g |
| Microcrystalline cellulose | 40 g |
| Hydroxypropyl cellulose low-substituted | 62 g |
| Disodium hydrogen phosphate | 2 g |
| Purified water | q.s. |

The active compound was mixed with the dry ingredients and granulated with a solution of disodium hydrogen phosphate. The wet mass was forced through an extruder and spheronized and dried in a fluidized bed dryer.

500 g of the pellets above were first coated with a solution of hydroxypropyl methylcellulose, 30 g, in water, 750 g, using a fluidized bed coater. After drying, the pellets were coated with a second coating as given below:

Coating Solution:

| | |
|---|---|
| Hydroxypropyl methylcellulose phthalate | 70 g |
| Cetyl alcohol | 4 g |
| Acetone | 200 g |
| Ethanol | 600 g |

The final coated pellets were filled into capsules.

Suppositories

Suppositories were prepared from the following ingredients using a welding procedure. Each suppository contained 40 mg of active compound.

| | |
|---|---|
| Compound according to Example 4 | 4 g |
| Witepsol H-15 | 180 g |

The active compound was homogenously mixed with Witepsol H-15 at a temperature of 41° C. The molten mass was volume filled into pre-fabricated suppository packages to a net weight of 1.84 g. After cooling the packages were heat sealed. Each suppository contained 40 mg of active compound.

BIOLOGICAL EFFECTS

Bioavailability

Biovailability is assessed by calculating the quotient between the area under plasma concentration (AUC) curve following intreduodenal (id) administration and intravenous (iv) administration from the rat.

Potency for Inhibition of Acid Secretion

The potency for inhibition of acid secretion is measured in the dog, intravenously (iv) and in the female rat, intravenously (iv).

Effects on the Uptake of Iodine into the Thyroid Gland

The effect of a compound within the invention of the formula I on the uptake of iodine into the thyroid gland is measured as an effect on the accumulation of $^{125}I$ in the thyroid gland.

BIOLOGICAL TESTS

Inhibition of Gastric Acid Secretion in the Conscious Female Rat

Female rats of the Sprague-Dawley strain are used. They are equipped with cannulated fistulae in the stomach (lumen) for collection of gastric secretions. A fourteen days recovery period after surgery is allowed before testing is commenced.

Before secretory tests, the animals are deprived of food but not water for 20 h. The stomach is repeatedly washed through the gastric cannula, and 6 ml of Ringer-Glucose given s.c. Acid secretion is stimulated with infusion during 3.5 h (1.2 ml/h, s.c.) of pentagastrin and carbachol (20 and 110 nmol/kg h, respectively), during which time gastric secretions are collected in 30-min fractions. Test substances or vehicle are given iv at 90 min after starting the stimulation, in a volume of 1 ml/kg. Gastric juice samples are titrated to pH 7.0 with NaOH, 0.1 mol/L, and acid output is calculated as the product of titrant volume and concentration. Further calculations are based on group mean responses from 4–7 rats. The acid output during the periods after administration of test substances or vehicle are expressed as fractional responses, setting the acid output in the 30-min period preceding administration to 1.0. Percentage inhibition is calculated from the fractional responses elicited by test compound and vehicle. $ED_{50}$-values are obtained from graphical interpolation on log dose-response curves, or estimated from single-dose experiments assuming a similar slope for all dose-response curves. The results are based on gastric acid secretion during the second hour after drug/vehicle administration.

Bioavailability in the Male Rat

Male adult rats of the Sprague-Dawley strain were used. One day, prior to the experiments, all rats were prepared by cannulation of the left carotid artery under anaesthesia. The rats used for the intravenous experiments, were also cannulated in the jugular vein. (Ref. V. Popovic and P. Popovic, J Appl Physiol 1960;15,727–728). The rats used for the intraduodenal experiments, were also cannulated in the upper part of the duodenum. The cannulas were exteriorized at the nape of the neck. The rats were housed individually after surgery and were deprived of food, but not water, before administration of the test substances. The same dose (4 μmol/kg) were given iv and id as a bolus for about one minute (2 ml/kg).

Blood samples (0.1–0.4 g) were drawn repeatedly from the carotid artery at intervals up to 4 hours after given dose. The samples were frozen as soon as possible until analysis of the test compound.

The area under the blood concentration vs time curve, AUC, was determined by the linear trapezoidal rule and extrapolated to infinity by dividing the last determined blood concentration by the elimination rate constant in the terminal phase.

The systemic bioavailability (F %) following intraduodenal administration was calculated as $$F(\%) = \frac{AUC_{id}}{AUC_{iv}} \times 100$$

Inhibition of Gastric Acid Secretion in the Conscious Dog

Harrier dogs of either sex were used. They were equipped with a duodenal fistula for the administration of test compounds or vehicle and a Heidenhain-pouch for the collection of gastric secretions.

Before secretory tests the animals were fasted for about 18 h but water was freely allowed. Gastric acid secretion was stimulated by a 4 h infusion of histamine dihydrochloride (12 ml/h) at a dose producing about 80% of the individual maximal secretory response, and gastric juice collected in consecutive 30-min fractions. Test substance or vehicle was given iv 1 h after starting the histamine infusion, in a volume of 0.5 ml/kg body weight. The acidity of the gastric juice samples were determined by titration to pH 7.0, and the acid output calculated. The acid output in the collection periods after administration of test substance or vehicle were expressed as fractional responses, setting the acid output in the fraction preceding administration to 1.0. Percentage inhibition was calculated from fractional responses elicited by test compound and vehicle. $ED_{50}$-values were obtained by graphical interpolation on log dose—response curves, or estimated from single-dose experiments under the assumption of the same slope of the dose-response curve for all test compounds. All results reported are based on acid output 2 h after dosing.

Effect on the Accumulation of $^{125}I$ in the Thyroid Gland

The accumulation of $^{125}I$ in the thyroid gland was studied in male, Sprague-Dawley rats which were deprived of food for 24 hours before the test. The experimental protocol of Searle, C. E. et al. (Biochem J 1950, 47:77-81) was followed.

Test substances suspended in 0.5% buffered (pH 9) methocel, were administered by oral gavage in a volume of 5 ml/kg body weight. After 1 hour, $^{125}I$ (300 kBqkg, 3 ml/kg) was administered by intraperitoneal injection. Four hours after $^{125}I$-administration, the animals were killed by $CO_2$-asphyxiation and bled. The thyroid gland together with a piece of the trachea was dissected out and placed in a small test tube for the assay of radioactivity in a gamma counter (LKB-Wallac model 1282 Compugamma). Percentage inhibition was calculated according to the formula 100 (1-T/P), where T and P is the mean radioactivety of thyroid glands from animals treated with test agent and placebo (buffered methocel), respectively. The statistical significane for a difference between test agent- and placebo-treated animals was assessed with the Mann-Whitney U-test (two-tailed). $P<0.05$ was accepted as significant.

Chemical Stability

The chemical stability of a compound of the invention is followed kinetically at low cencentration at 37° C. in aqueous buffer solution at different pH values. The results in Table 4 show the half life (t ½) at pH 7, that is the time period after which half the amount of the original compound remains unchanged.

Results of Biological and Stability Tests

Table 4 gives a summary of the test data available for the compounds of the invention.

TABLE 4

| | Biological Test Data and Stability Data | | | | |
|---|---|---|---|---|---|
| Test compound Example No. | Inhibition of acid secretion iv administration $ED_{50}$ μmol/kg | | Bioavailability F %, Rat | Percent inhibition of 400 μmol/kg on the uptake of $^{125}I$ in the thyroid gland | Chemical stability at pH 7 half-life (t ½) min |
| | Dog | Rat | | | |
| 2 | | a) | | | |
| 3 | 0.5 | | | 0 | 480 |
| 4 | 0.74 | 0.9 | >100 | −7 | 470 |
| 5 | | | | −6 | 270 | a) 1 μmol/kg gave 14% inhibition

We claim:

1. A compound of the Formula I

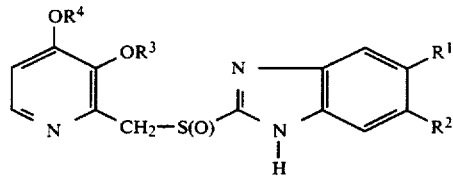

or a physiologically acceptable salt thereof wherein $R^1$ is —C(O)OCH₃ and $R^2$ is $CH^3$
and
$R^3$ and $R^4$ are each $CH_3$.

2. The magnesium salt of a compound according to claim 1.

3. The sodium salt of a compound according to claim 1.

4. A pharmaceutical composition effective in inhibiting gastric acid secretion in mammals including man, containing as an active ingredient a compound according to claim 1, together with a pharmaceutically acceptable carrier.

5. A pharmaceutical composition for use in therapy of gastrointestinal inflammatory diseases in mammals including man, containing as an active ingredient a compound according to claim 1, together with a pharmaceutically acceptable carrier.

6. A method for inhibiting gastric acid secretion in mammals including man, comprising administering to said mammals an effective amount of a compound as defined in claim 1 in either an oral, rectal or parenteral pharmaceutical formulation.

7. A method for the treatment of gastrointestinal inflammatory diseases in mammals including man, comprising administering to said mammals an effective amount of a compound as defined in claim 1 in either an oral, rectal or parenteral pharmaceutical formulation.

* * * * *